(12) United States Patent
Boykin et al.

(10) Patent No.: US 10,952,908 B2
(45) Date of Patent: Mar. 23, 2021

(54) WATERPROOF MENSTRUAL PAD

(71) Applicants: Rita Rose Johnson Boykin, Wilson, NC (US); Kenneth Ray Boykin, Sr., Wilson, NC (US)

(72) Inventors: Rita Rose Johnson Boykin, Wilson, NC (US); Kenneth Ray Boykin, Sr., Wilson, NC (US)

( * ) Notice: Subject to any disclaimer, the term of this patent is extended or adjusted under 35 U.S.C. 154(b) by 112 days.

(21) Appl. No.: 16/363,176

(22) Filed: Mar. 25, 2019

(65) Prior Publication Data

US 2019/0298585 A1  Oct. 3, 2019

Related U.S. Application Data

(60) Provisional application No. 62/651,118, filed on Mar. 31, 2018.

(51) Int. Cl.

| | | |
|---|---|---|
| *A61F 13/475* | (2006.01) | |
| *A61F 13/472* | (2006.01) | |
| *A61F 13/534* | (2006.01) | |
| *A61F 13/513* | (2006.01) | |
| *A61F 13/514* | (2006.01) | |
| *A61F 13/47* | (2006.01) | |

(52) U.S. Cl.
CPC ........ *A61F 13/4755* (2013.01); *A61F 13/472* (2013.01); *A61F 13/4758* (2013.01); *A61F 13/51305* (2013.01); *A61F 13/534* (2013.01); *A61F 2013/4708* (2013.01); *A61F 2013/5147* (2013.01)

(58) Field of Classification Search
CPC ................ A61F 13/4755; A61F 13/494; A61F 13/4752; A61F 13/4757; A61F 13/476; A61F 13/4751; A61F 13/4758; A61F 13/4753; A61F 2013/4944; A61F 2013/4708; A61F 13/534
See application file for complete search history.

(56) References Cited

U.S. PATENT DOCUMENTS

| | | | |
|---|---|---|---|
| 2003/0114805 A1* | 6/2003 | Rainville-Lonn | A61F 13/74 604/358 |
| 2010/0312216 A1* | 12/2010 | Periman | A61F 13/4758 604/385.04 |
| 2014/0228796 A1* | 8/2014 | Burvall | A61F 13/494 604/385.01 |

\* cited by examiner

*Primary Examiner* — Tatyana Zalukaeva
*Assistant Examiner* — Heather K Barnwell
(74) *Attorney, Agent, or Firm* — The Iwashko Law Firm, PLLC; Lev Ivan Gabriel Iwashko

(57) ABSTRACT

A waterproof menstrual pad having an outer portion to contact a woman's underwear and an inner portion to contact a groin area of the woman, the waterproof menstrual pad including an absorbent portion disposed at a center portion of an inner surface of the inner portion to absorb blood, and an outer-edge waterproof lining disposed along an outer edge of the inner surface of the inner portion to prevent water from entering the inner surface.

3 Claims, 2 Drawing Sheets

WATERPROOF MENSTRUAL PAD

CROSS REFERENCE TO RELATED APPLICATION

This application claims the benefit of, and incorporates by reference, U.S. provisional patent application Ser. No. 62/651,118, entitled "Waterproof Menstrual Pad," which was filed on Mar. 31, 2018.

BACKGROUND

1. Field

The present general inventive concept relates generally to a menstrual pad, and particularly, to a waterproof menstrual pad.

2. Description of the Related Art

Many women are not able to enter any body of water during their menstrual cycles, due to their fear of blood leakage during the physical act of swimming. This hinders their ability to enjoy normal activities with their friends and family, and causes them to have to miss out on fun and memorable experiences.

Therefore, there is a need for a menstrual pad that allows women to swim during their menstrual cycles, without worrying about blood leakage.

SUMMARY

The present general inventive concept provides a waterproof menstrual pad.

Additional features and utilities of the present general inventive concept will be set forth in part in the description which follows and, in part, will be obvious from the description, or may be learned by practice of the general inventive concept.

The foregoing and/or other features and utilities of the present general inventive concept may be achieved by providing a waterproof menstrual pad having an outer portion to contact a woman's underwear and an inner portion to contact a groin area of the woman, the waterproof menstrual pad including an absorbent portion disposed at a center portion of an inner surface of the inner portion to absorb blood, and an outer-edge waterproof lining disposed along an outer edge of the inner surface of the inner portion to prevent water from entering the inner surface.

The waterproof menstrual pad may further include a plurality of inner side waterproof linings disposed on the inner surface between the absorbent portion and side edges of the outer-edge waterproof lining.

The waterproof menstrual pad may further include a plurality of inner end waterproof linings disposed on the inner surface between the absorbent portion and end edges of the outer-edge waterproof lining.

The waterproof menstrual pad may further include an adhesive surface disposed on the outer portion.

The foregoing and/or other features and utilities of the present general inventive concept may also be achieved by providing a waterproof menstrual pad, including an outer surface to contact a woman's underwear, and an inner portion to contact a groin area of the woman, the inner portion including an absorbent portion disposed on the inner portion, and an outer-edge waterproof lining disposed along an outer edge of the inner portion to prevent water from entering the inner portion.

BRIEF DESCRIPTION OF THE DRAWINGS

These and/or other features and utilities of the present generally inventive concept will become apparent and more readily appreciated from the following description of the embodiments, taken in conjunction with the accompanying drawings of which.

DETAILED DESCRIPTION

Various example embodiments (a.k.a., exemplary embodiments) will now be described more fully with reference to the accompanying drawings in which some example embodiments are illustrated. In the figures, the thicknesses of lines, layers and/or regions may be exaggerated for clarity.

Accordingly, while example embodiments are capable of various modifications and alternative forms, embodiments thereof are shown by way of example in the figures and will herein be described in detail. It should be understood, however, that there is no intent to limit example embodiments to the particular forms disclosed, but on the contrary, example embodiments are to cover all modifications, equivalents, and alternatives falling within the scope of the disclosure. Like numbers refer to like/similar elements throughout the detailed description.

It is understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art. However, should the present disclosure give a specific meaning to a term deviating from a meaning commonly understood by one of ordinary skill, this meaning is to be taken into account in the specific context this definition is given herein.

Figure 1:
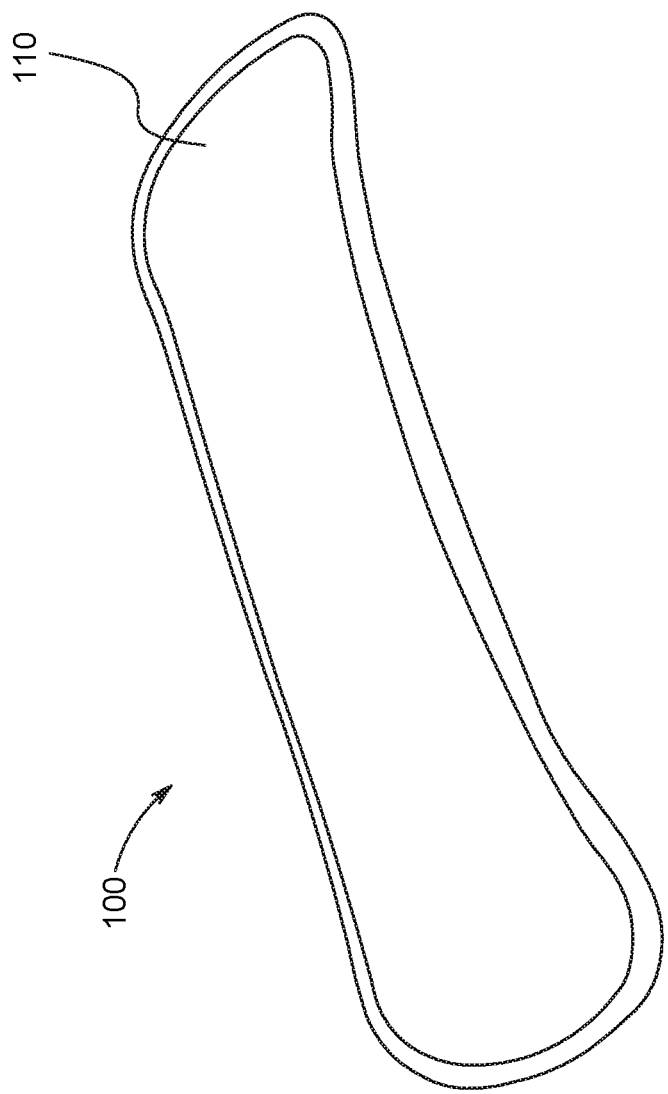
FIG. 1 illustrates a top angled view of an outer portion of a waterproof menstrual pad, according to an exemplary embodiment of the present general inventive concept.

FIG. 1 illustrates a top angled view of an outer portion (i.e., back, rear) of a waterproof menstrual pad 100, according to an exemplary embodiment of the present general inventive concept.

Figure 2:
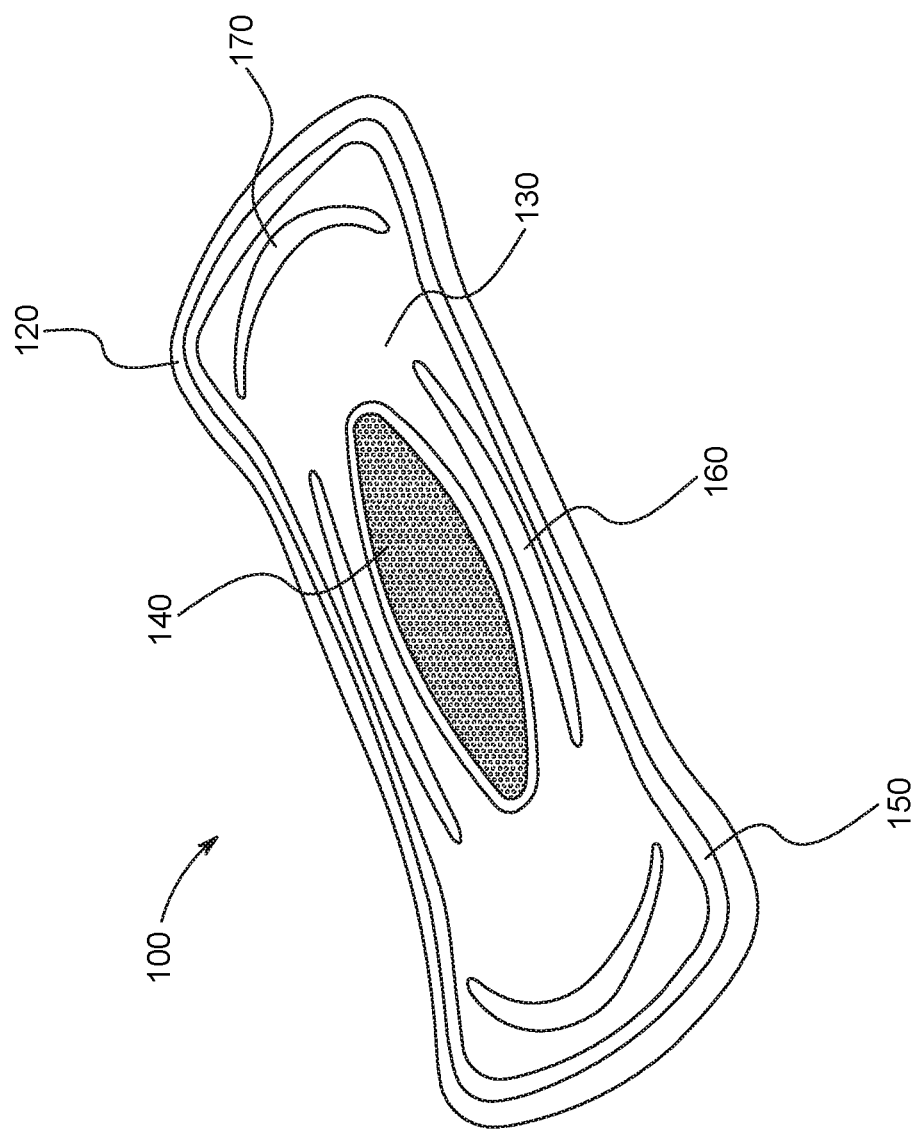
FIG. 2 illustrates a top angled view of an inner portion of a waterproof menstrual pad, according to an exemplary embodiment of the present general inventive concept.

FIG. 2 illustrates a top angled view of an inner portion of the waterproof menstrual pad 100, according to an exemplary embodiment of the present general inventive concept.

As such, the outer portion of the waterproof menstrual pad 100 may contact a woman's underwear and the outer portion of the waterproof menstrual pad 100 may contact a groin area (i.e., crotch, genitalia) of the woman.

The waterproof menstrual pad 100, and components thereof, may be constructed from flexible material such as, paper, rubber, silicone, plastic, cotton, fabric, rayon, etc., but are not limited thereto.

Referring to FIG. 1, the outer portion of the waterproof menstrual pad 100 may include an adhesive surface 110 disposed on the outer portion thereof. The adhesive surface 110 may be a temporary adhesive that may include waterproof properties, such that if the adhesive surface becomes wet, the adhesive surface 110 does not lose its adhesive properties.

The adhesive surface 110 may be a portion of the waterproof menstrual pad 100 that contacts an inner portion of a woman's underwear, such that the waterproof menstrual pad 100 adheres to the inner portion of the woman's underwear. As such, the adhesive surface 110 may allow the waterproof menstrual pad 100 to remain securely in place within the woman's underwear.

Referring to FIG. 2, the inner portion of the waterproof menstrual pad 100 may include an edge portion 120, an inner surface 130, an oval-shaped absorbent portion 140, an outer-edge waterproof lining 150, a plurality of inner side waterproof linings 160, and a plurality of inner end waterproof linings 170.

The edge portion 120 may be disposed at an outermost edge of the waterproof menstrual pad 100, and may outline an entirety of the outermost edge of the waterproof menstrual pad 100.

The inner surface 130 may be disposed inside the outermost edge of the waterproof menstrual pad 100, that is, within the edge portion 120. In other words, the edge portion 120 may completely surround the inner surface 130.

The absorbent portion 140 may be disposed in and/or on a center portion of the inner surface 130. The size of the absorbent portion 140 is less than the size of the inner portion. The absorbent portion 140 may be constructed from absorbent material and/or chemicals that help the absorbent portion 140 absorb a flow of blood emerging from a woman's vagina when the woman wears the waterproof menstrual pad 100.

The absorbent portion 140 may vary in thickness and size, based on a preference of a user. More specifically, the absorbent portion 140 may have a thinner/smaller size for women with a light menstrual flow, and the absorbent portion 140 may have a thicker/larger size for women with a heavy menstrual flow.

The outer-edge waterproof lining 150 may be disposed near the edge portion 120 of the waterproof menstrual pad 100, and may divide the edge portion 120 from the inner surface 130.

The outer-edge waterproof lining 150 may be constructed from waterproof material, such as rubber or plastic, to prevent water from entering the inner surface 130. More specifically, when the woman is wearing the waterproof menstrual pad 100 while in a swimming pool, for example, the outer-edge waterproof lining 150 may prevent the water from entering an area of the inner surface 130.

The plurality of inner side waterproof linings 160 and the plurality of inner end waterproof linings 170 may be constructed from waterproof material, such as rubber or plastic, to further prevent water from entering the inner surface 130.

The plurality of inner side waterproof linings 160 may be disposed at side portions of the waterproof menstrual pad 100, particularly between side portions of the outer-edge waterproof lining 150 and the absorbent portion 140. The plurality of inner side waterproof linings 160 are concave shaped with respect to the oval-shaped absorbent portion 140, such that a length of the plurality of inner side waterproof linings 160 is less than a length of the absorbent portion 140. The plurality of inner end waterproof linings 170 may be disposed at top and bottom end portions of the waterproof menstrual pad 100, particularly between top and bottom end portions of the outer-edge waterproof lining 150 and the absorbent portion 140. Each of the plurality of inner end waterproof linings 170 are concave shaped with respect to the oval-shaped absorbent portion 140, such that each of the plurality of inner end waterprool linings 170 are concave shaped differently with respect to each other.

As such, a combination of the waterproof lining 150, the plurality of inner side waterproof linings 160, and the plurality of inner end waterproof linings 170, provides extra protection from water entering the inner surface 130, while also preventing blood accumulated in the absorbent portion 140 from exiting an area of the inner surface 130.

Although a few embodiments of the present general inventive concept have been shown and described, it will be appreciated by those skilled in the art that changes may be made in these embodiments without departing from the principles and spirit of the general inventive concept, the scope of which is defined in the appended claims and their equivalents.

The invention claimed is:

1. A waterproof menstrual pad having an outer portion configured to contact a woman's underwear and an inner portion configured to contact a groin area of the woman, the waterproof menstrual pad comprising:
    an oval-shaped absorbent portion disposed at a center portion of an inner surface of the inner portion configured to absorb blood, such that a size of the oval-shaped absorbent portion is less than a size of the inner portion;
    an outer-edge waterproof lining disposed along an outer edge of the inner surface of the inner portion configured to prevent water from entering the inner surface;
    a plurality of inner side waterproof linings disposed on the inner surface between the oval-shaped absorbent portion and side edges of the outer-edge waterproof lining, such that the plurality of inner side waterproof linings are concave shaped with respect to the oval-shaped absorbent portion, such that a length of the plurality of inner side waterproof linings is less than a length of the oval-shaped absorbent portion to provide extra protection from water entering the inner surface; and
    a plurality of inner end waterproof linings disposed on the inner surface between the oval-shaped absorbent portion and top and bottom end edges of the outer-edge waterproof lining, such that each of the plurality of inner end waterproof linings are concave shaped with respect to the oval-shaped absorbent portion, such that each of the plurality of inner end waterproof linings are concave shaped differently with respect to each other to provide extra protection from water entering the inner surface.

2. The waterproof menstrual pad of claim 1, further comprising:
   an adhesive surface disposed on the outer portion.

3. A waterproof menstrual pad, comprising:
   an outer surface configured to contact a woman's underwear; and
   an inner portion configured to contact a groin area of the woman, the inner portion comprising:
   an oval-shaped absorbent portion disposed on the inner portion, such that a size of the oval-shaped absorbent portion is less than a size of the inner portion;
   an outer-edge waterproof lining disposed along an outer edge of the inner portion configured to prevent water from entering the inner portion;
   a plurality of inner side waterproof linings disposed on the inner surface between the oval-shaped absorbent portion and side edges of the outer-edge waterproof lining, such that the plurality of inner side waterproof linings are concave shaped with respect to the oval-shaped absorbent portion, such that a length of the plurality of inner side waterproof linings is less than a length of the oval-shaped absorbent portion to provide extra protection from water entering the inner surface; and
   a plurality of inner end waterproof linings disposed on the inner surface between the oval-shaped absorbent portion and top and bottom end edges of the outer-edge waterproof lining, such that each of the plurality of inner end waterproof linings are concave shaped with respect to the oval-shaped absorbent portion, such that each of the plurality of inner end waterproof linings are concave shaped differently with respect to each other to provide extra protection from water entering the inner surface.

* * * * *